United States Patent [19]

Wyatt et al.

[11] 4,101,383

[45] * Jul. 18, 1978

[54] PROCESS FOR TESTING MICROPARTICLE RESPONSE TO ITS ENVIRONMENT

[75] Inventors: Philip J. Wyatt; Vincent R. Stull, both of Santa Barbara; William L. Proctor, Goleta, all of Calif.; Irving L. Miller, New Haven, Conn.

[73] Assignee: Science Spectrum, Inc., Santa Barbara, Calif.

[*] Notice: The portion of the term of this patent subsequent to Dec. 23, 1992, has been disclaimed.

[21] Appl. No.: 640,195

[22] Filed: Dec. 12, 1975

Related U.S. Application Data

[62] Division of Ser. No. 468,992, May 10, 1974, Pat. No. 3,928,140.

[51] Int. Cl.² .............................................. C12K 1/04
[52] U.S. Cl. ...................... 195/103.5 R; 195/103.5 A; 195/103.5 K; 195/103.5 M; 356/104
[58] Field of Search ................. 195/103.5 R, 103.5 K, 195/103.5 M, 103.5 A; 356/103, 104

[56] References Cited

U.S. PATENT DOCUMENTS 3,928,140  12/1975  Wyatt et al. ................. 195/103.5 R Primary Examiner—Lionel M. Shapiro
Assistant Examiner—Robert J. Warden
Attorney, Agent, or Firm—Spensley, Horn & Lubitz

[57] ABSTRACT

A differential light scattering photometer is disclosed for testing samples of bacteria in suspension. A plurality of cuvettes containing the samples are placed in a cuvette holder or carousel which rotatably places each cuvette in position to interrupt a laser beam. A detector rotates in an arc about each sample to produce output signals representing the scattered light intensity as a function of angular location, relative to the incident laser beam, about the sample. A control differential scattering pattern is produced and compared with test differential scattering patterns derived from test samples having added antibiotics. The patterns are compared by data processing to produce an output punched card indicative of bacterial sensitivity to each antibiotic. The data processor is responsive, through pattern comparison, to various responses of the bacteria, i.e., whether the antibiotic is bactericidal, bacteriostatic or the bacteria actually metabolize the antibiotic. An appropriate protocol and process is disclosed.

26 Claims, 6 Drawing Figures

PROCESS FOR TESTING MICROPARTICLE RESPONSE TO ITS ENVIRONMENT

This is a division of application Ser. No. 468,992, filed May 10, 1974 now U.S. Pat. No. 3,928,140.

The present invention is directed to the use of differential light scattering patterns in general to test the response of a microparticle to its environment. More particularly the invention is directed to testing bacterial response to chemical and chemotherapeutic agents. More especially the invention is directed to bacterial sensitivity or susceptibility to antibiotics.

Expressly incorporated by reference herein are the following co-pending Patent Application and Patents having a common assignee:
U.S. Pat. No.: 3,624,835
Title: Microparticle Analyzer Employing a Spherical Detector Array
Inventor: Philip J. Wyatt
Date of Issue: Nov. 30, 1971
U.S. Pat. No.: 3,770,351
Title: Optical Analyzer for Microparticles
Inventor: Philip J. Wyatt
Date of Issue: Nov. 6, 1973
U.S. Pat. No.: 3,730,842
Title: Process for Determining Bacterial Drug Sensitivity
Inventor: P. J. Wyatt et al.
Date of Issue: May 1, 1973
U.S. Pat. No.: 3,701,620
Title: Sample Scattering Cell for a Photometer
Inventor: R. M. Berkman et al.
Date of Issue: Oct. 31, 1972
U.S. Pat. No.: 3,754,830
Title: Scattering Cell Employing Electrostatic Means for Supporting a Particle
Inventor: D. T. Phillips et al.
Date of Issue: Aug. 28, 1973
Co-pending Application Ser. No. 139,366
Title: Light Scattering Photometer Recorder Unit
Inventor: H. H. Brooks et al.
Date of Filing: May 3, 1971

In addition the following publication is expressly incorporated herein by reference: In the book Methods in Microbiology, Volume 8, edited by J. R. Norris and D. W. Ribbons, Academic Press, published in 1973, Chapter VI entitled "Differential Light Scattering Techniques for Microbiology" and authored by Philip J. Wyatt, one of the inventors herein.

DEFINITIONS

The term differential scattering pattern means a radiant energy or light scattering pattern derived from the measurement of the intensity of scattered radiation or light as a function of angular location with respect to an incident beam illuminating a scatterer or scatterers. At least a plurality of measurements taken at a plurality of discrete angular locations is required to establish the pattern; i.e., a plurality of measurements of the intensity as a function of a plurality of discrete angles. A sufficient number of such measurements and, therefore, angular locations is required to extract an indication of selected properties of the scatterer or scatterers. Such properties include the number of scatterers, the shape of the scatterer, the dielectric structure, refractive index or indices, size and/or size distribution.

The term microparticle or microparticles as used herein, includes but is not limited to, particles ranging in size from 0.1 micron to 10 microns in at least one dimension.

The term biologically derived microparticle or microparticles, as used herein, includes but is not limited to a microparticle or microparticles of organic compounds which comprise, form a constituent of or duplicate in whole or in part biologically active matters, whether or not synthesized, such as mammalian cells, microorganisms, viruses, macromolecules, antigens, antibodies, amino acids, RNA, DNA, molecules, or emulsions.

THE INVENTION — BRIEF DESCRIPTION

A differential light scattering photometer is described and illustrated below for testing samples of bacteria in suspension. A plurality of cuvettes containing the samples are placed in a cuvette holder or carousel which rotatably places each cuvette in position to interrupt a laser beam. A detector rotates in an arc about each sample to produce signals representing the scattered light intensity as a function of angular location, relative to the incident laser beam, about the sample. A logarithmic amplifier is coupled to the detector to provide output signals representing the logarithm of the scattered light intensity. The output signals are converted from analog to digital form and stored as data bits from which a differential scattering pattern is derived. A control differential scattering pattern is derived from a control bacterial sample and compared with test differential scattering patterns derived from test bacteria samples having added antibiotics. The patterns are compared by data processing to produce an output punched card indicative of bacterial sensitivity to each antibiotic. The data processor is responsive, through pattern comparison, to various responses of the bacteria; i.e., whether the antibiotic is bactericidal, bacteriostatic or the bacteria actually metabolize the antibiotic.

A protocol for the test for determining bacterial sensitivity to antibiotics has been developed which uses a 20–50% standard broth diluted with water.

Minimum inhibitory concentrations of antibiotics or other chemical or chemotherapeutic agents are determined by using a modification of the apparatus and process of the invention.

Bioassay or the determination of the presence and/or amount of an antibiotic, chemotherapeutic or chemical agent is accomplished with a variation of the apparatus and process by utilizing bacterial strains of known and calibrated response to a given antibiotic, chemotherapeutic or chemical agent.

PRIOR ART — BACTERIAL TESTING

The conventional turbidimetric or nephelometric tests for bacterial sensitivity to antibiotics may misinterpret a change in the average size of bacteria as a change in the number of bacteria. Both tests use a control sample of bacteria alone and a test sample of bacteria with an added antibiotic. Healthy bacteria are characterized by growth in the number of bacteria which increases turbidity (turbidimetric) or scattering at a single angular location (nephelometric). If both control and test samples continue to grow at substantially the same rate, no change between the control and test samples is indicated. This is interpreted as finding the bacteria resistant to the antibiotic. More particularly such tests cannot distinguish between an increase in the number of scatterers in the control medium and an increase in the size of the scatterers with the number remaining substantially constant in the test medium. An increase in the size of the bacteria without increase in number indicates a bacteriostatic condition, i.e., no multiplication and indeed meets the definition of being sensitive to the antibiotic. Thus it is highly desirable in the measurement of sensitivity to include a function which is extremely sensitive to the change in relative structures of the scatterers.

In the event that the number of both test and control particles remains substantially constant, and there is a negligible average size change, the conventional test interpretation is that the bacteria are resistant. This kind of problem typically occurs in the case of bacteria having a long generation time. Mycobacterium tuberculosis, for example, multiplies so slowly that turbidity changes may not be observed for days or even weeks depending on the inoculum size. In the test sample, however, sensitive bacteria undergo subtle structural changes which indeed result in a change in the shape of the corresponding differential scattering pattern relative to the control pattern.

As is well known, anaerobic bacteria cannot grow in the presence of free oxygen. Thus when anaerobic sensitivities are tested turbidimetrically or nephelometrically in the presence of oxygen both control and test samples may die and both will certainly cease to multiply. Since there would be no multiplication of the control relative to the test, the turbidities would remain the same, indicating resistance.

An anaerobe introduced into an aerobic environment also containing an antibiotic to which it is sensitive undergoes subtle structural changes more pronounced than those of a control suspension thereby yielding a changed differential scattering pattern relative to the control even though there has been no multiplication of either test or control.

Differential Scattering Pattern is a Function of the Properties of the Particles The differential scattering pattern derived from a microparticle or a collection of microparticles, as in a suspension or solution, is a function of the particles' physical properties such as number, average shape, average dielectric structure, average size, and size and shape distributions. Any change of any of these properties of the microparticle or microparticles in response to a given environmental change can produce a corresponding change in the differential scattering pattern.

Size and Number of Particles

In the preferred embodiment the test measurement is a function of the logarithm of the intensity of scattered light. As will be described below, the logarithm of intensity is substantially undistorted relative to a uniform change of intensity. Hence, in the preferred embodiment and process of the invention, a change in the size of the single microparticle under test in general effect an apparent linear displacement between the corresponding test and control differential scattering patterns and a change in the shape of the differential scattering pattern, as well. For a collection of microparticles a change in the relative number of particles has a greater effect on the apparent displacement between the patterns than a small change in average size. This is particularly true of bacteria because size changes are always relatively small during the period of the preferred test situation relative to their changes in number. However, as noted above, there are a number of very important situations involving no change in number of particles with only a change in other structural parameters. It will be apparent that a change in the number or size of the particles increases the volume of scattering material and, in general if these changes are large enough, the intensity of the scattered light, producing in accordance with the preferred mode herein an apparent linear displacement between the control and test differential scattering patterns in addition to a change of pattern shape.

Other and further considerations of the invention will be apparent from the following description of the invention, taken in connection with the accompanying drawings and its scope will be pointed out in the appended claims.

IN THE DRAWINGS

PRINCIPLES OF THE INVENTION — FIG. 1

Figure 1:
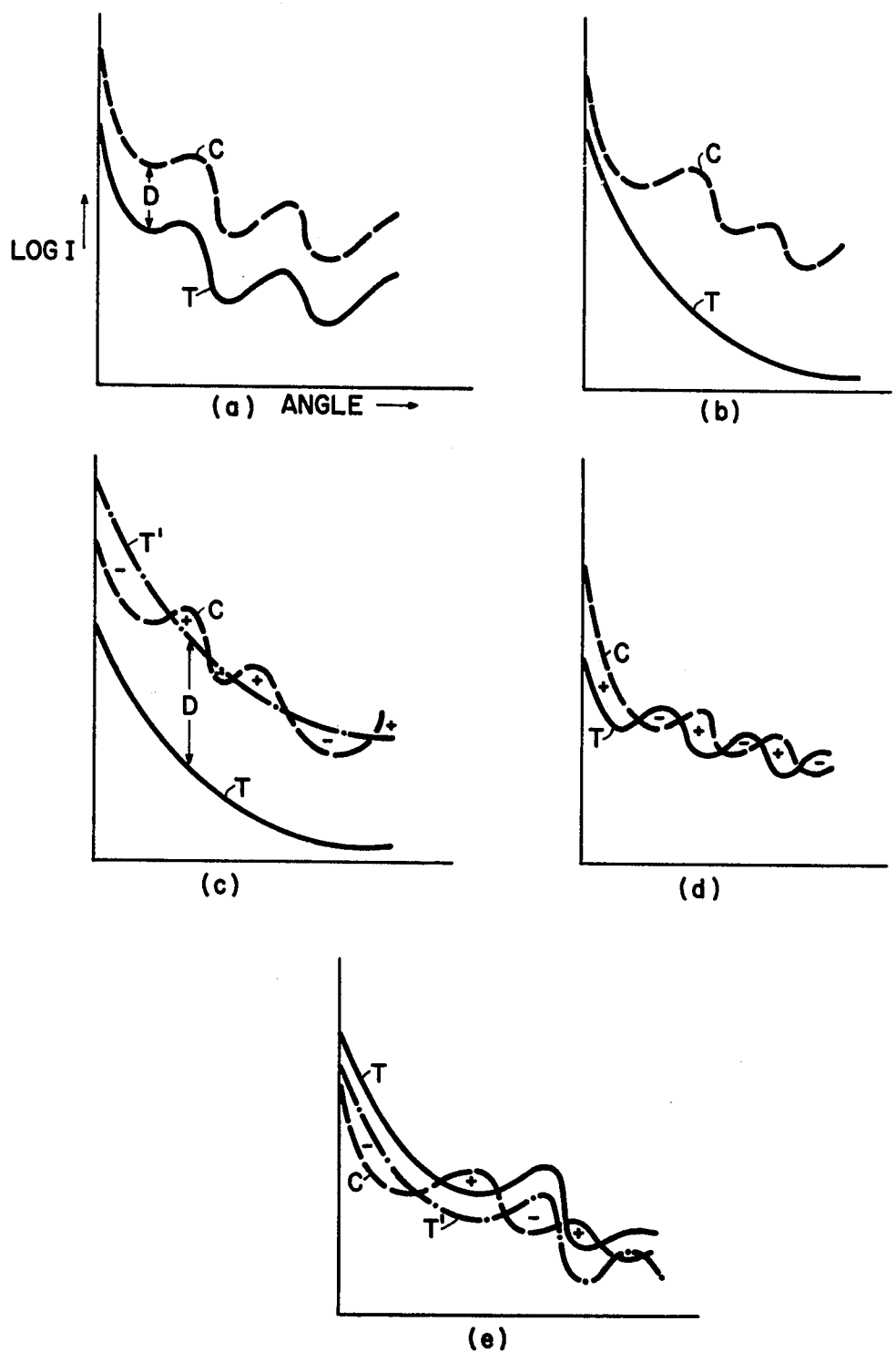
FIG. 1 is a series of graphs $(a)$–$(e)$ illustrating the differential scattering patterns of the invention.

The principles of the invention will be discussed with reference to the patterns illustrated in the graphs $(a)$ – $(e)$ illustrated in FIG. 1. A test differential scattering pattern on a logarithmic scale produced by sample microparticles varies in displacement and shape relative to a control differential scattering pattern on a logarithmic scale in accordance with the properties of the test scatterer relative to the control scatterer. More particularly the resultant pattern in displacement and shape is a function of the properties of the scatterers such as their number, size distribution, average shape, the distribution of shapes, the average size, and average refractive index structure. The mean displacement of the pattern is primarily a function of the number of particles and secondarily a function of the average size of the particles. The shape of the pattern is a function of other parameters, mainly size distribution, average size, average dielectric structure, and distribution of particle shapes and sizes. The dependence of the pattern shape on particle number is generally greater than is true of the dependence of the pattern displacement on particle size. In the prior application, Serial No. 139,366 there is disclosed an algorithm for comparing a control differential scattering pattern of bacteria with a test differential scattering pattern produced by bacteria treated with an antibiotic. The algorithm is of the form $$S = \frac{A - B}{A} = 1 - \frac{B}{A}, \qquad \text{Eqn. (1)}$$

where

A = the 'slope' of the control pattern derived by subtracting the first minimum value from the first following maximun value, and B = the first minimum value of the test pattern subtracted from the first following maximum value of the test pattern.

It will be apparent that so long as no multiple scattering occurs within the suspensions such an algorithm is independent of the mean displacement between the control and test patterns, and really is a function of only those properties of the scatterers which affect the shape of the patterns. If the curve is of the form shown in FIG. 1(a) where the shape of the control pattern and test pattern are essentially the same, such an algorithm would hold that the two patterns are identical when in fact they are displaced. Another algorithm suggested in the 139,366 application is to take the ratio of the two patterns. More particularly quoting from that application on Page 26, Lines 4–10, "The output from the photomultiplier tube, therefore, represents the light-scattering properties of the sample at the different angular positions. This signal, as indicated above, may be directly recorded on a chart recorder or may be used by comparing this signal to a control signal and providing for an output signal representative of the ratio between the two signals."

The ratio between the curves representing the control and test patterns is itself a function of the angular location at which the intensity is measured. Thus the statement in the 139,366 application suggests an algorithm of the form $$S = R(\theta) = \frac{C(\theta)}{T(\theta)}, \quad \text{Eqn. (2)}$$

where indeed S is a function rather than a number representative of the differences between the curves.

On Lines 16–19 of Page 26 of application 139,366, there is the concept of integrating the area between the control and test patterns. This suggests an algorithm of the form $$S = \int_{\theta_1}^{\theta_2} [C(\theta) - T(\theta)]d\theta. \quad \text{Eqn. (3)}$$

This algorithm of itself is useful in testing certain bacteria for some antibiotics. It is also useful in determining the mean displacement between the control and test patterns. As the sole basis for the indication of bacterial sensitivity, however, it has been found to be too limited in application for the entire range of bacteria and antibiotics of clinical interest.

THE ALGORITHM OF THE PREFERRED MODE

The following discussion is based on the control pattern C and test pattern T as functions of the logarithm of the measured intensity of scattered light. Thus $$C = \log I_C(\theta) \text{ and} \quad \text{Eqn. (4)}$$

$$T = \log I_T(\theta), \quad \text{Eqn. (5)}$$

where

C = control pattern derived from a control sample,
T = test pattern derived from a test sample, and $I(\theta)$ = the measured intensity of scattered light as a function of angular location $\theta$, about the sample, relative to an incident light beam.

The importance of using the logarithm is discussed in the referenced publication authored by Wyatt. Quoting from Chapter VI entitled "Differential Light Scattering Techniques", "4. Effect of cell density on logarithmic plots "The differential light scattering patterns from suspensions of cells are often most conveniently recorded on a logarithmic scale. This tends to compress the vertical excursions of the recorded patterns while at the same time compensating for modest changes in cell numbers. This latter fact is clearly evident from the following brief discussion".

"In order to predict the differential scattered light intensity that would be recorded from an ensemble of scattering cells we must integrate over the distribution present. If $\rho(D)$, as before, represents the number of cells with diameters between D and D + dD and if there are $N_0$ cells per unit volume, then $$N_0 = \int_0^\infty \rho(D)dD \quad (9)$$

$$= N_0 \int_0^\infty g(D)dD$$

where $\rho(D) = N_0 g(D)$ and $g(D)$ is a normalized distribution function such that $$\int_0^\infty g(D)dD = 1. \quad (10)$$

"Consider now the differential light scattering pattern that the ensemble of $N_0$ cells/ml would produce. If a cell of diameter D yields the pattern $I(\theta,D)$, the superimposed pattern would be simply $$I(\theta) = \int_0^\infty \rho(D)I(\theta,D)dD \quad (11)$$

$$= N_0 \int_0^\infty g(D)I(\theta,D)dD.$$

If we now plot log $[I(\theta)]$ vs $\theta$, we obtain the important result $$\log[I(\theta)] = \log[N_0 \xi(\theta)]$$

$$= \log N_0 + \log \xi(\theta),$$

where $$\xi(\theta) = \int_0^\infty g(D)I(\theta,D)dD. \quad (12)$$

Equation (12) shows that if we plot the logarithm of the differential scattering pattern, the shape of the scattering pattern will be independent of the number of cells/ml, $N_0$, since the only effect of number density variation is the vertical displacement (proportional to log $N_0$) of the scattering pattern. This independence of shape upon the number of cells present is not true for linear plots. In addition, even in the logarithmic plotting mode it will remain true, only if multiple scattering is not present at any of the concentrations, $N_0$, being studied. Implicit also is the assumption that the distribution itself does not vary with concentration. Evidence exists which shows that the distribution does indeed change as cells pass from their "lag" phase, through exponential phase, into stationary phase. This change, though, is usually not so great as to invalidate Eqn. (12)."

Thus, the differential scattering pattern as used here is derived from the logarithm of the measured value and $$I_i' = \log I_i(\theta) \quad \text{Eqn. (5a)}$$

defines the $i^{th}$ value of the intensity of the $i^{th}$ angular location. It will be shown below by another approach that for a change in the number of particles, all other factors being substantially the same, the measured change between the control and test patterns appears as a linear displacement parallel to the ordinate or logarithmic axis. Let $I(\theta,\phi)$ be the intensity light scattered from $n_o$ particles. The intensity is indicated as a function of the solid angle to be most general and not limit the discussion to scattering in a plane. There is a description of the sizes, shapes, and orientation with respect to the incident beam of the particles $$n(R,s,\alpha) = n_o \xi(R,s,\alpha) \quad \text{Eqn. (5b)}$$

where R is the average radius, $s$ is a shape factor, and $\alpha$ is a vector direction in space along a defined axis of the particle relative to the direction of the incident beam. The intensity of the incident beam is $I_o$ and the scattering cross-section of the particle of average radius R, shape $s$, and orientation $\alpha$ is $$\sigma(\theta,\phi,R,s,\alpha). \quad \text{Eqn. (5c)}$$

The intensity of the light scattered by the ensemble is $$I(\theta,\phi) = \quad \text{Eqn. (5d)}$$
$$\int dR \int ds \int d\alpha I_o n_o \sigma(\theta,\phi,R,s,\alpha)\xi(R,s,\alpha) = n_o I_o \beta(\theta,\phi).$$

$$\beta(\theta,\phi) = \int dR \int ds \int d\alpha \, \sigma \xi$$

Hence $$\log [I(\theta,\phi)] = \log [n_o I_o \beta(\theta,\phi)] = \log n_o + \log [I_o \beta(\theta,\phi)], \quad \text{Eqn. (5e)}$$

where $$\int dR \int ds \int d\alpha \, \xi(R,s,\alpha) = 1, \quad \text{Eqn. (5f)}$$

and the integrals span the ranges of the indicated variables. Thus a change in $n_o$ yields only a linear shift in $\log[I(\theta,\phi)]$ and the shape of the pattern is unaffected.

If there is a change in the relative shapes between the control and test patterns, a change in the shape, dielectric structure or indices of refraction, size and/or size distribution of the scattering particles is implied.

As noted above, while the change in the average size of the particles may result in the shift of the test pattern relative to the control pattern, for many applications such as bacteria testing, the size changes are relative very small during the period tested and contribute negligibly to such a shift.

The response of a collection of microparticles to a given test environment is best quantified by considering changes in the number of particles separately from other structural and size distribution changes. The separation or apparent displacement between the patterns is first determined by comparing the control and test patterns as shown for example is FIG. 1(b). The second step is to determine the displacement, D, necessary effectively to shift the curve vertically as shown in FIG. 1(c) to eliminate the linear displacement between them. Finally the shifted test curve is compared with the control curve. A scalar figure of merit indicative of the sensitivity or response, S, to a change in the environment of the particle may be derived in a number of ways. Whatever method for deriving S is chosen it must relate to and be a function of those pattern characteristics which indeed are derived from changes in the properties of the scatterers.

The differential scattering pattern inherently includes sufficient information on the properties of the scatterers to provide a basis for comparing control and test patterns for determining the response of a microparticle or microparticles to an environmental change. As noted above the derivation or role of the linear displacement factor, i.e. the displacement between the mean values of the patterns, is a direct measure of a change in the number of particles in the test sample. Shifting the test pattern vertically as in FIG. 1(c) to achieve a shifted pattern T' in such a manner that the algebraic sum of the area between the curves is zero enables a direct measure to be derived of the changes in the other parameters discussed above.

There are many possible analytical methods for comparing the control and test patterns. Such methods include but are not limited to comparison of areas, slopes, inflection points, amplitudes and so forth. Such comparisons may be accomplished by a number of mathematical methods involving various types of arithmetic operations referred to the curves, their derivatives, various sums and integrals, harmonic analyses, polynomial analyses, and so forth. It is another matter however to define a useful algorithm which produces a scalar quantity, for example, as a measure of the degree of response of a particle to its environment in terms of changes in the properties of the scatterer or scatterers caused by the environment. In the particular application of bacterial response to chemical, chemotherapeutic or antibiotic agents, the question to be answered is whether or not the agent is present in the sample or is effective for a particular purpose. For antibiotics it is important to know whether or not a given pathogenic strain of bacteria can be therapeutically treated to inhibit an infection. Either an antibiotic is useful for inhibiting an infection or it is not. It is often important to distinguish amoung four conditions: (1) Is the antibiotic bactericidal, i.e. does it act by killing cells? (2) Is the antibiotic bacteriostatic, i.e. does it act by just stopping multiplication? (3) Are the bacteria resistant to the antibiotic, i.e. are they unaffected by it? or even (4) Are the bacteria dependent upon a particular antibiotic, i.e. do the bacteria require the antibiotic for growth? The most useful algorithm for sensitivity testing then should be cognizant of all of these conditions.

In addition to the above considerations it is important to note that for a reliable and reproducible test as to the response of a microparticle to a change in its environment a given algorithm when implemented electronically can be confused or distorted by the presence of noise. The dependence of the algorithm on extraordinarily stable devices included as components within the system is a major factor. If such dependence is too great the method may become impractical.

With regard to the present invention, if $C_i$ are the set of control logarithms of the scattered light intensity values $I_{C_i}$ taken at the angular locations $i$, and $T_i$ are the set of test logarithms of the scattered light intensity values $I_{T_i}$ taken at the angular locations $i$, the departure of the test differential scattering pattern relative to the control may most generally be described by $$S = f(C_i, T_i),\qquad \text{Eqn. (6)}$$

where S is preferably a scalar quantity indicative of the sensitivity or response of the microparticle or microparticles to a change in their environment. A ratio of the form $$R = \frac{f(C,T_i)}{f(C,C_i)} \qquad \text{Eqn. (7)}$$

is also a comparison in the sense of the invention in that the ratio departs from unity as the test pattern departs from the control pattern, almost irrespective of the form of $f$.

Another form of the comparison involves the sum or difference of two function, one of which might reflect the average difference between the sets $C_i$ and $T_i$ while the other might reflect the difference between the sets $C_i$ and a modified set $T_i'$, where $$T_i' = O[T_i], \qquad \text{Eqn. (8)}$$

where O is a generalized operator that transforms for each $i$ the value $T_i$ into another value $T_i'$. For example, the functional operator O may simply represent a displacement between the patterns and would therefore yield $$T_i' = O[T_i] = T_i + D, \qquad \text{Eqn. (9)}$$

where D is a constant representing the difference between the mean value of $C_i$ and the mean value of $T_i$. The two function comparison might thus be of the form $$f(C_i, T_i) = K_1 g(C_i, T_i) + K_2 g(C_i, T_i'), \qquad \text{Eqn. (10)}$$

where $K_1$ and $K_2$ are constants and $g(x_i, y_i)$ is a function of the sets $x_i$ and $y_i$.

Let us consider now some specific examples of the types of algorithms of the aforementioned forms.

For the ratio form exemplified by Eqn. (7) one could have $$R_1 = \frac{\sum\limits_{i=1}^{n} C_i T_i}{\sum\limits_{i=1}^{n} (C_i)^2}, \qquad \text{Eqn. (11)}$$

where $n$ is the total number of points recorded representative of the differential light scattering patterns. Again, $$R_2 = \frac{\sum\limits_{i=1}^{n}(C_i + T_i)}{\sum\limits_{i=1}^{n} 2 C_i}, \qquad \text{Eqn. (12)}$$

or $$R = \frac{\Sigma C_i T_i - \frac{1}{n}\Sigma C_i \Sigma T_i}{\sqrt{[\Sigma C_i^2 - \frac{1}{n}(\Sigma C_i)^2][\Sigma T_i^2 - \frac{1}{n}(\Sigma T_i)^2]}} \qquad \text{Eqn. (13)}$$

(this is the so-called correlation coefficient) or even a complex form of the type $$R_3 = \frac{\sum\limits_{i=1}^{n} \tanh(C_i + T_i)}{\sum\limits_{i=1}^{n} \tanh(2 C_i)} \qquad \text{Eqn. (14)}$$

where $\tanh x$ is the hyperbolic tangent of $x$.

For the functional form of the type exemplified by Eqn. (10), one could have $$f(C,T) = K_1 \sum_{i=1}^{n} |C_i - T_i| + K_2 \sum_{i=1}^{n} |C_i - T_i'|, \qquad \text{Eqn. (15)}$$

where $T_i' = T_i + D$ and $D = \dfrac{1}{p-q+1} \sum\limits_{i=q}^{p}(C_i - T_i)$, where $p$ and $q$ may be further selected so long as $q$ is less than or equal to $p$ which is less than or equal to $n$, or even such forms as $$f(C,T) = K_1 \sum_{i=1}^{n}(C_i - T_i)^2 + K_2 \sum_{i=1}^{n}(C_i - T_i')^2, \qquad \text{Eqn. (16)}$$

and all terms are defined as above.

It will be appreciated that for subsequent analytical manipulation it is often useful to replace the sets of discrete points $C_i$ and $T_i$ by continuous functions of the angular variable, $\theta$. For example, each differential light scattering pattern could be represented by a variety of equivalent expansions in orthogonal polynomials of the angular variable. A particularly useful representation would involve the replacement of the differential light scattering patterns by expansions in terms of Chebyshev polynomials [M. A. Snyder, Chebyshev Methods in Numerical Approximation (Prentice-Hall, Englewood Cliffs, New Jersey, 1966); C. Lanczos, Applied Analysis (Prentice Hall, Englewood Cliffs, New Jersey)]. Consider the set of points $C_i (i = 1, 2, \ldots, n)$ where $n$ is the number of points recorded, $C_1$ = value of control curve at the first recorded angle, $C_2$ = value of control curve at the second recorded angle, ... and $C_k$ = value of control curve at the $k^{th}$ recorded angle.

Let $m = i - 1$, $N = n - 1$, then the control points may be represented in the form $C_m$ ($m = 0, 1, \ldots, N$). We now seek a polynomial approximation of order $p$ (less than N) of the differential scattering pattern $$C(\theta) = \xi_p(\theta) = \sum_{m=0}^{p} a_m f_m(\theta) \qquad \text{Eqn. (17)}$$

where $f_m(\theta)$ is the modified Chebyshev polynomial of order $m$, $\theta$ is in degrees, and the polynomials satisfy the recurrence relation $$(k+1)(N-k)f_{k+1}(\theta) = (2k+1)(N-2\theta)f_k(\theta) - k(N+k+1)f_{k-1}(\theta)$$

$$f_o(\theta) = 1$$

$$f_1(\theta) = 1 - 2\theta/N.$$

The coefficients $a_m$ are functions of all the $N+1$ recorded points and are readily generated (loc. cit.) using standard procedures involving the various analytical properties of the polynomials.

Thus the control differential scattering pattern may be represented by $$C(\theta) \simeq \xi_p(\theta) = \sum_{m=0}^{N} a_m f_m(\theta) \quad \text{Eqn. (18)}$$

and the test differential scattering pattern by $$T(\theta) \simeq \xi_p(\theta) = \sum_{m=0}^{N} b_m f_m(\theta). \quad \text{Eqn. (19)}$$

Note that in such a representation the coefficients $a_j$ and $b_j$ are independent and are only functions of the recorded points $C_i$ and $T_i$ respectively. By eliminating higher values of $p$, the higher frequency noise contributions may be effectively filtered, i.e. removed. If $T(\theta)$ and $C(\theta)$ differ only by a displacement D in addition to some random noise fluctuations, then one could shift one curve relative to the other so as to yield a minimum difference between the first few expansion coefficients. The differences between the remaining coefficients might then be used as a measure of the departure of one curve relative to the other.

Numerous other comparisons between the curves may be made by considering various combinations of the coefficients, for example $$\sum_{m=0}^{N} (a_m - b_m)$$

$$\sum_{m=0}^{N} (a_m - b_m)^2, \text{ etc.,}$$

and all the aforementioned types of algorithms whereby the smoothed values $C_i$ and $T_i$ are represented by the sets $a_m$ and $b_m$, respectively.

Refer now to FIG. 1. There is here illustrated in graph FIG. 1(a) a control and test pattern which are substantially identical shifted only vertically by an average displacement D. For example, a strain of Pseudomonas aeruginosa sensitive to the antibiotic chloramphenicol might produce such a pair of test and control curves in accordance with the test of the invention. FIG. 1(d) represents somewhat idealized curves for a sensitive Staphylococcus aureus suspension prepared in accordance with the protocol outlined below, with the test specimen exposed to 0.1 μg/ml ampicillin. FIG. 1(c) illustrates the shift of the test pattern T to eliminate the displacement D and produce a new test pattern T'. FIG. 1(b) again illustrates in idealized form a test in accordance with the invention involving Pseudomonas bacteria sensitive to the antibiotic gentamicin in accordance with the preferred embodiment of the invention.

The Present Algorithm

The present algorithm used is generally of the form $$S = K_1 A + K_2 B, \quad \text{Eqn. (20)}$$

where
$K_1$ is a constant,
$K_2$ is a constant,
A is of the form $$A = \int_{\theta_1}^{\theta_4} |C(\theta) - T(\theta)|\, d\theta, \text{ and} \quad \text{Eqn. (21)}$$

B is of the form $$B = \int_{\theta_1}^{\theta_4} |C(\theta) - T'(\theta)|\, d\theta \quad \text{Eqn. (22)}$$

where $T' = T + D$, and $$D = \frac{\int_{\theta_2}^{\theta_3} [C(\theta) - T(\theta)]\, d\theta}{\theta_3 - \theta_2} \quad \text{Eqn. (23)}$$

where $\theta_1 \leq \theta_2 \leq \theta_3 \leq \theta_4$.

Algorithm as Modified for the Preferred Embodiment

In the preferred embodiment, the curves derived from the photodetector are converted to a digital representation and a pattern of discrete points is obtained for each angular location $i$ so that the pattern C is the set of all points $C_i$, the pattern T is the set of all points $T_i$ and the pattern T' is the set of all points $T_i'$. The equations (21), (22), and (23) noted above are approximated as follows:

$$A = \sum_{i=1}^{m} |C_i - T_i|$$

where
$m$ = the number of angular locations,
A = the absolute area between said patterns without shifting,
$C_i$ = the $i^{th}$ value of the control pattern at the $i^{th}$ angular location,
$T_i'$ = the $i^{th}$ value of the test pattern at the $i^{th}$ angular location, $$B = \sum_{i=1}^{m} |C_i - T_i|$$

where
B = the absolute area between said patterns after shifting,
$T_i' = T_i + D$,
where $$D = \frac{1}{n-q+1} \sum_{i=q}^{n} (C_i - T_i)$$

or any of its algebraic equivalents, where
D = the average relative displacement between said patterns, q = the first angular location used to calculate D,
n = the last angular location used to calculate D, and
$1 \leq q \leq n \leq m$, A scalar quantity indicating the sensitivity of a given bacterial test sample to a given antibiotic is thus given by S. In the preferred embodiment, as described and illustrated above, Equation (20) is often found most useful in the form $$S = A + 3B \qquad \text{Eqn. (20')}$$

indicating that $K_1 = 1$ and $K_2 = 3$.

In Equations (20) and (20') for A and B above, the first angular position, $i=1$ is often chosen in the 25° to 35° range. Approximately 100 points at one degree intervals is found to be particularly useful.

FIG. 1(e) shows a situation where T is above C which implies that D is negative. This rare but important occurence suggests that the bacteria as noted above may be antibiotic dependent and may in fact require the presence of the antibiotic for metabolism. Such "superresistant" strains are often associated with the antibiotic streptomycin. A negative D may also arise because of faulty sample preparation, i.e. too many bacteria may inadvertently have been added to one or more of the test cuvettes. In that event D is negative. This negative D situation gives rise in the preferred embodiment to a special indication which effectively drops the dependence of S on the A term completely. If D is more negative than might be expected from the statistical fluctuations of noise, this situation implies a superresistant situation or faulty preparation and the preferred embodiment yields a special value for S (00) indicating this.

APPARATUS FOR TESTING BACTERIAL SENSITIVITY TO ANTIBIOTICS AS ILLUSTRATED IN FIGS. 2-6

Figure 2:
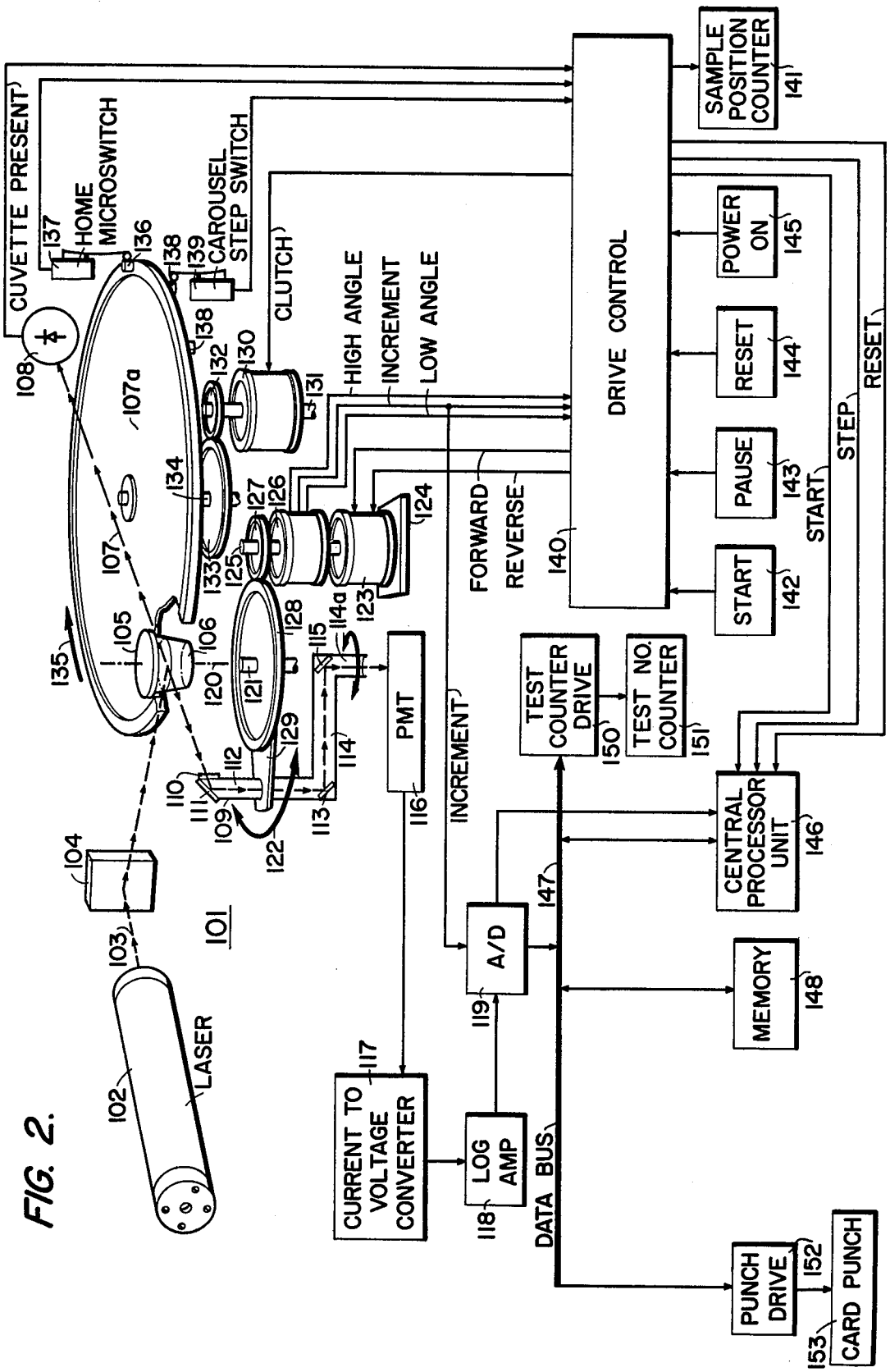
FIG. 2 is a schematic, partially fragmented, partially exploded view in perspective and block diagram of the preferred apparatus for testing bacterial sensitivity to antibiotics.

Referring now to the drawings and with particular reference to FIG. 2, there is here illustrated a differential light scattering pattern photometer for practicing the test for the response of a microparticle to a change in its environment. More particularly, the preferred embodiment is described and illustrated herein with respect to the test for determining bacterial sensitivity to an antibiotic.

The apparatus as illustrated generally includes a laser light source, a circular carousel or sample holder with a cuvette and sample shown in place, a rotatable periscope for receiving scattered light through a small fixed solid angle from the sample over a continuous range of angular locations and a drive and drive control. The periscope directs scattered light to a stationary photodetector coupled to a logarithmic amplifier and then to an analog-to-digital converter which provides digital signals to a central processing unit, a memory, a card punch, a test number counter and a drive control circuit for the periscope and the carousel.

The apparatus is generally indicated at 101. A laser 102 produces an incident narrow, coherent, substantially monochromatic beam of preferably vertically polarized light along an optical axis 103 to a mirror 104. The beam is directed to a cuvette 105 described in reference U.S. Pat. No. 3,701,620. The cuvette contains a bacterial sample 106 in fluid suspension. A carousel or sample holder 107a receives the sample cuvette for placement into the path of the beam 103.

The beam 103 is refracted by fluid 106 to direct a beam 107 at a refracted angle to a photodetector 108 which produces a signal indicating the presence of a cuvette. Without the cuvette and fluid sample the beam 103 is not refracted and no light impinges on the photocell 108. The carousel and cuvette are more particularly illustrated in FIG. 5 to be described in greater detail below.

The light from the sample 106 is scattered in all directions. At the angular location shown, the periscope 109 receives the scattered light from the sample through an input aperture 110. The light is reflected by a mirror 111 downwardly as shown through the first vertical leg 112 to a mirror 113 through a horizontal section 114 to a mirror 115 downwardly through the second vertical leg 114a and an output aperture to a photodetector, here shown as a photomultiplier tube 116.

The output of the photomultiplier tube is coupled through a current-to-voltage conversion amplifier 117 to a logarithm amplifier 118 which is coupled to an analog-to-digital signal converter 119. The periscope 109 is driven about an axis 120 defined by a drive shaft 121 about an angular range 122, for example in the range 30°-130°, with respect to the direction of the incident beam 103. A scanner motor 123 mounted on a base 124 is coupled through a drive shaft 125 to an optical encoder 126, and drive wheel 127 coupled through a drive wheel 128 to a support arm 129 for the periscope 109.

A carousel motor 130 is coupled through a drive shaft 131 through a carousel drive wheel 132 to a second carousel drive wheel 133. The wheel 133 is coupled to a drive shaft 134 to the carousel which normally rotates in a clockwise direction as indicated by the arrow 135. An upper detent bearing 136 is fixed to the carousel for engaging a home microswitch 137 when the carousel table is in the home or zero sample test position. The zero sample test position corresponds with the control sample.

Lower detent bearings 138 engage a carousel table step switch 139. While two of the members 138 are shown in the preferred embodiment there are ten such detent bearings distributed circumferentially at equal angles around the carousel table. The switches 137 and 139 are coupled to a drive control 140. The drive control 140 is further coupled to the optical encoder 126 and scanner motor 123. A sample position counter 141 is coupled to the drive control 140. Manual controls START 142, PAUSE 143, RESET 144, and POWER ON 145 are coupled to the drive control 140.

The output of the analog-to-digital converter 119 is coupled to a central processor unit 146 and through a data bus 147 to a memory 148. The data bus 147 couples the central processor unit 146 to a test counter drive 150 which is coupled to a test number counter 151. The data bus 147 also couples the memory 148 and the central processor unit 146 to a punch drive interface 152. The output of the punch drive interface 152 is coupled to a card punch 153.

Figure 5:
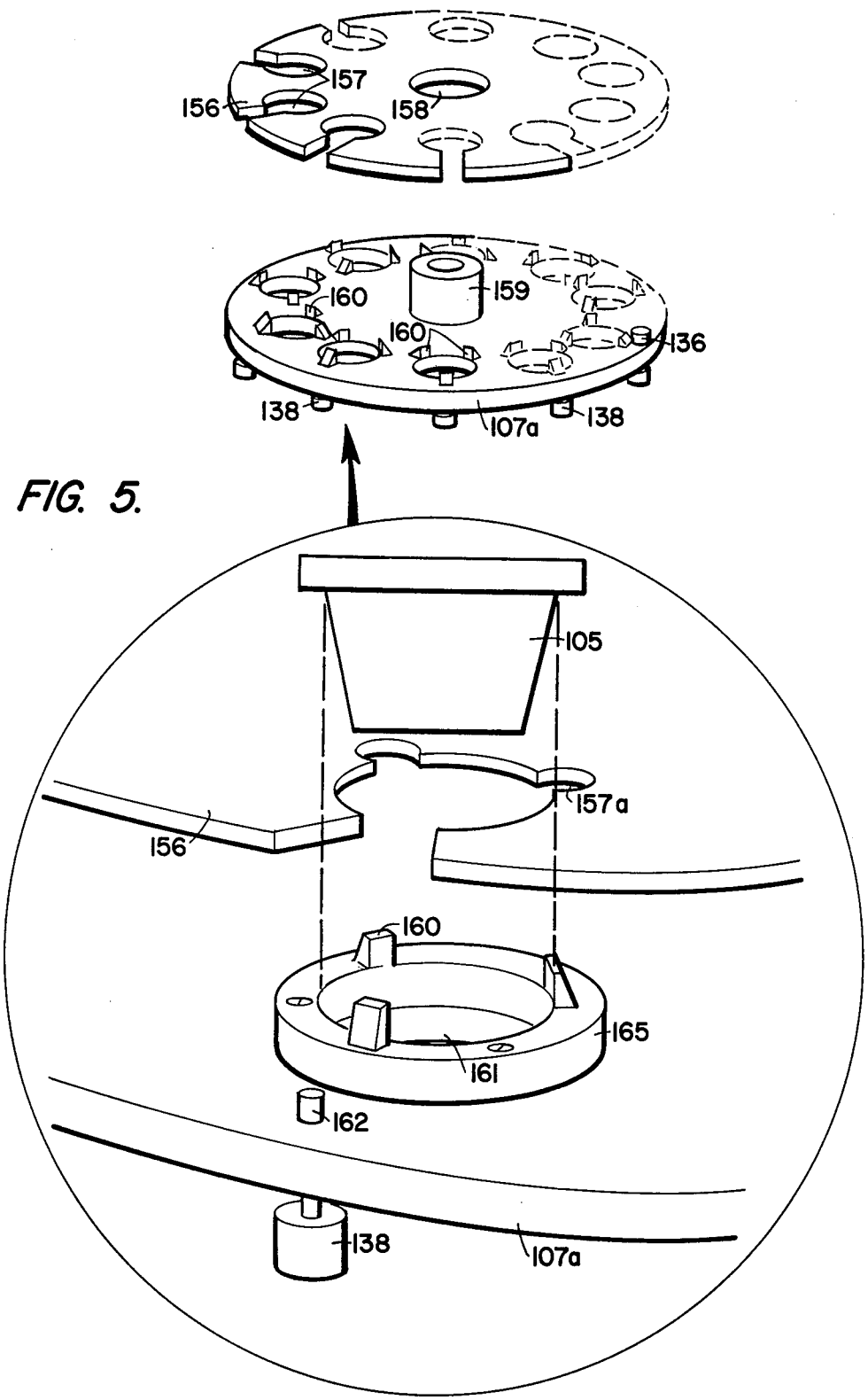
FIG. 5 is a fragmentary, detail, perspective view of a sample holder and tray as used in the apparatus in FIG. 2.

In FIG. 5 a carrying tray 156 is shown which is keyed (not shown) to engage the carousel sample holder 107a. As shown, there are 10 clearance holes 157 in the tray 156 to receive the cuvettes 105. Clearance holes 157a adjacently formed in the tray 156 receive pods 160, as noted below. The clearance hole 158 in the center of the tray 156 receives a fixed bearing 159 in the carousel 107a and enables the tray to drop into contact with the carousel table 107a. Tripod centering support posts or pods 160 surround each opening 161 in the carousel table 107a to receive and support each cuvette 105 in place. As shown the detent 138 for the table step switch is a roller bearing carried by a shaft 162. The home detent 136 is coupled to the shaft 162 for the step detent 138 in the home position.

Figure 6:
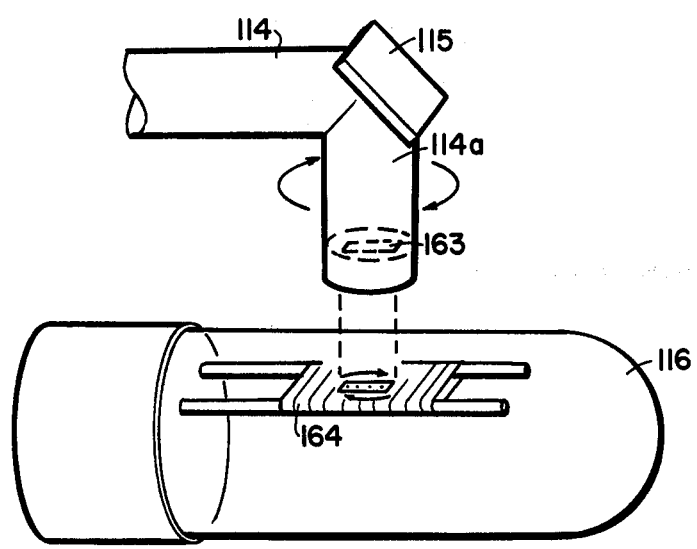
FIG. 6 is a fragmentary, partially perspective view of a periscope section and photodetector as used in the apparatus in FIG. 2.

In FIG. 6 there is a detail drawing showing the imaging of the output aperture 163 on the cathode grid 164 of the photomultiplier 116.

OPERATION — APPARATUS IN FIG. 2

Figure 3:
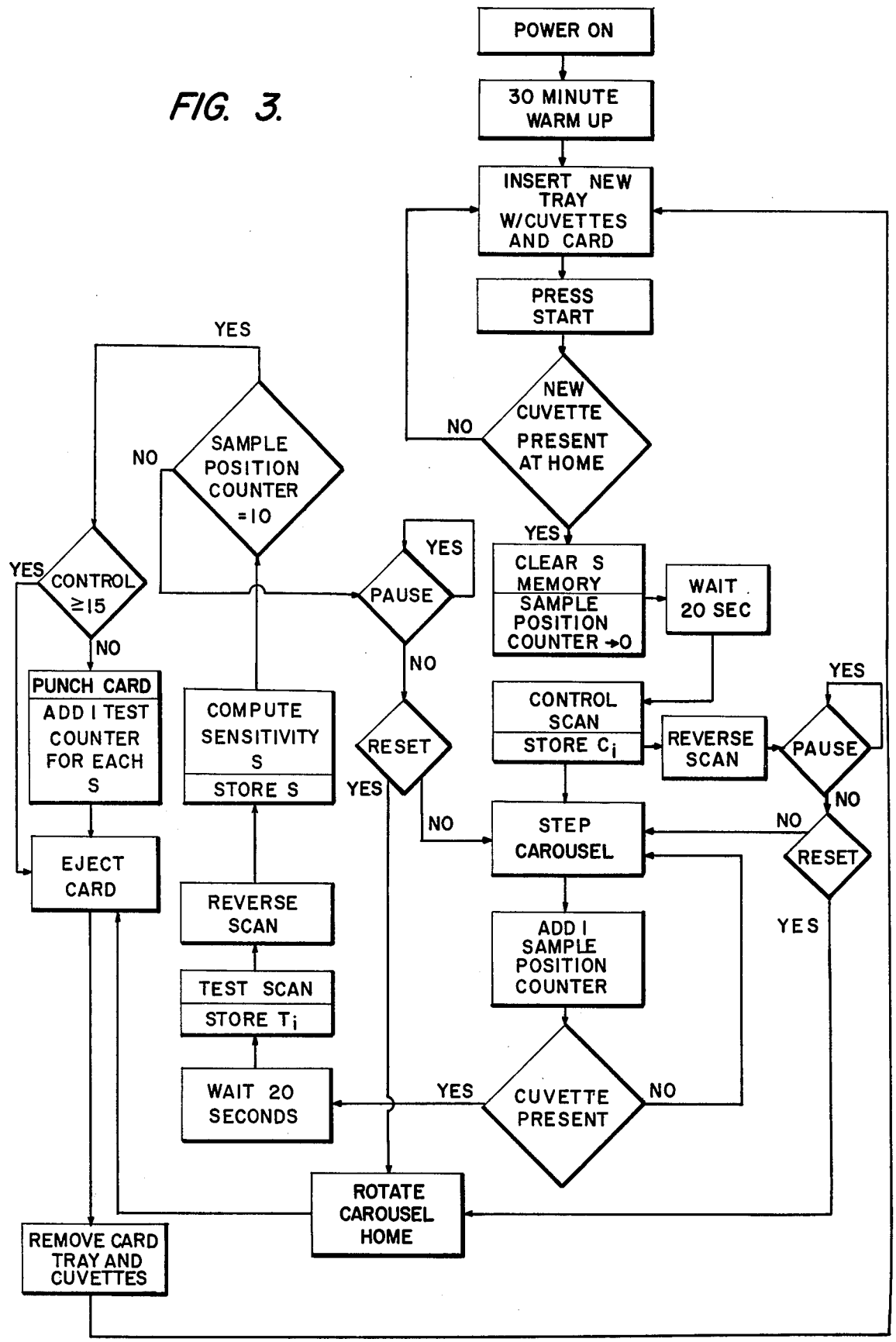
FIG. 3 is an operational flow diagram illustrating the operation of the apparatus in FIG. 2.

Referring now to FIG. 2 and to the operational flow diagram in FIG. 3, the POWER ON switch 145 is turned on. Power is applied to all power supplies (not shown) and all components are energized except the scanner motor 123. A 30 minute warm-up is desirable to enable the laser to stabilize. When a cuvette tray 156 is inserted in place on the carousel table 107a, the housing lid (not shown) is interlocked and must be closed, and a sensitivity S or score card is inserted in the card punch 153. The START button is pressed. If no cuvette is in place the motor control receives no signal from the photodiode 108. If the photodiode 108 presents a signal indicating the presence of a new cuvette, the start light goes on and the S memory is cleared. The sample position counter is set to zero indicating the control sample is in place. A delay circuit in the drive control 140 introduces a delay, for example of the order of five to 20 seconds, to allow the sample fluid to come to rest. After the delay a signal from the control drive circuit 140 energizes the scanner motor 123 forwardly to drive the periscope 109 from the low angle to the high angle. The optical encoder 126 produces signals in one degree increments indicative of the instantaneous position of the periscope 109. When it reaches the high angle position, a signal is coupled to the control drive 140 to reverse the scanner motor 123.

In the course of the forward scan the analog-to-digital converter 119 produces the desired number of data signals $C_i$ indicative of the control sample scattered light intensity at each angular location, for example 100°, which are then stored in the memory 148. After the reverse scan is accomplished and the periscope 109 is returned to its initial position, a signal in the control drive 140 is coupled through the PAUSE control 143 and the RESET control 144 to the clutch of the carousel motor 130 to cause it to step the carousel table 107a to the next or first test sample position and increment the sample position counter 141. A signal from the photodiode 108 indicates the presence of a new cuvette and again, after a five to 20 second delay, a signal from the control drive 140 energizes the scanner motor 123 in the forward direction and produces the desired number of signals indicative of the test sample scattered light intensity at each angular location. If the RESET control 144 has not been depressed, the central processor unit 146 computes the sensitivity, S, and stores it in the memory unit 148. If the sample position counter 141 is less than 10, an output in the control drive 140 is coupled through the PAUSE and RESET and is recirculated to rotate the table to its next position for the next test sample.

This continues until the sample position counter 141 reaches 10. Recall that the first position is zero so that the tenth count represents rescanning the control sample. The second control pattern derived is then compared with the stored control pattern to compute apparent sensitivity, but this is really a measure of the extent to which the control pattern has changed from its initial condition. The apparent sensitivity is now coupled through the sample position counter control circuit to a control which responds to a threshold sensitivity signal. If the apparent sensitivity is greater than or equal to the threshold value, the test is aborted. If, however, the two control patterns are within an acceptable low sensitivity score, for example less than or equal to 14, the score for each of the nine tests is punched out on a card and the test number counter 151 is incremented for each test score. When the test is completed the card is removed from the card punch 153 and the tray 156 is removed together with the cuvettes 105 in place. When the test is reinitiated the tray 156 with cuvettes 105 and card are replaced and a new set of cuvettes 105 are inserted.

The purpose of the RESET 144 is to enable the operator to abort the test in the event he discovers some disorder. The purpose of the PAUSE control 143 is to permit the introduction of a visual representation of the pattern by a recorder being introduced, for example an external interface such as an x–y plotter. In addition the PAUSE control is useful for checking any aspect of the test on the machine without aborting the test. Examples include noting the configuration of the cuvettes, inspecting the machine's operation, analyzing the test with regard to some parameter, or for maintenance.

PARTS LIST — FIGS. 2 AND 4

Figure 4:
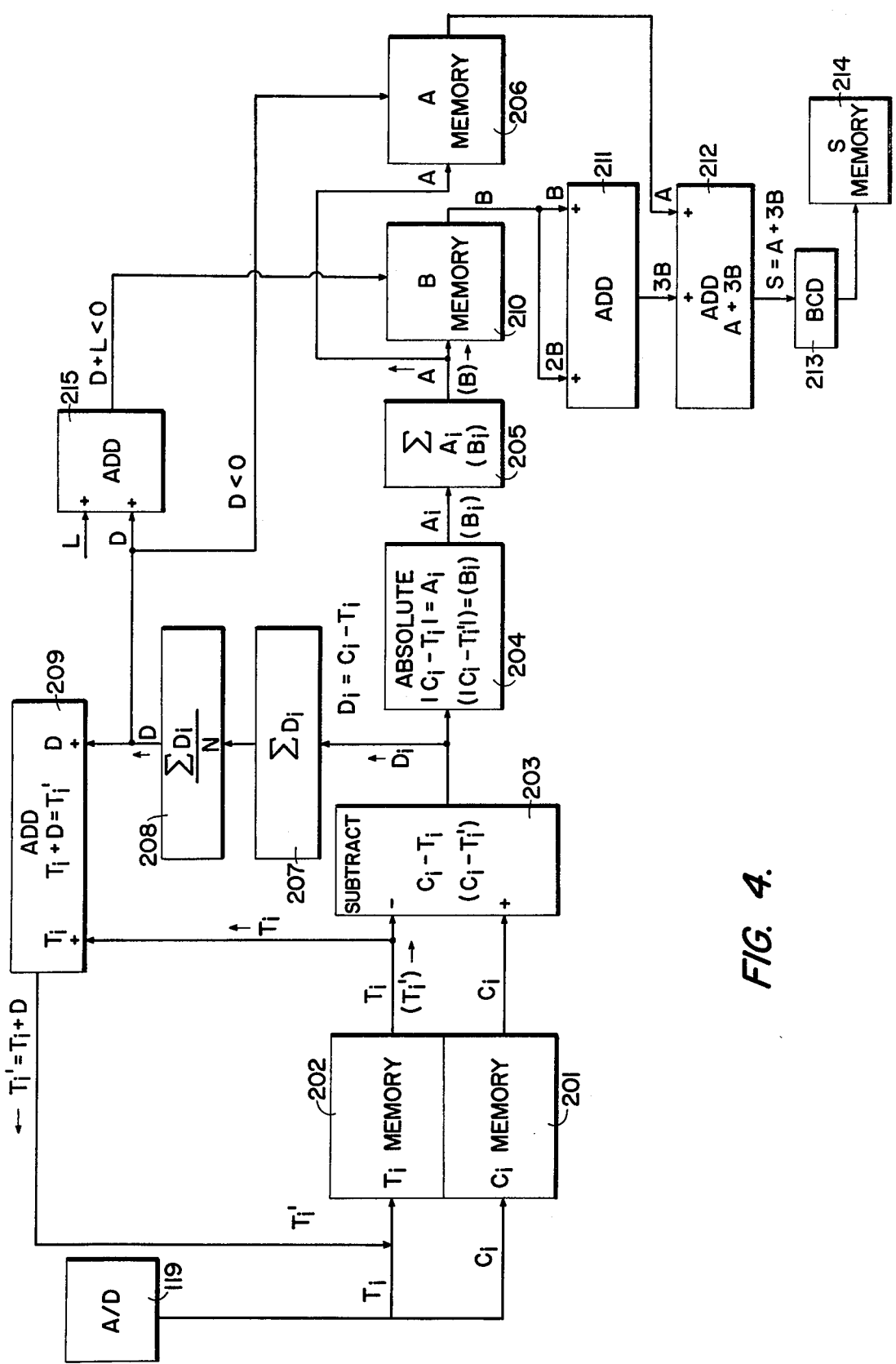
FIG. 4 is a schematic block diagram of a portion of the memory and central processing unit in FIG. 2 for deriving the control and test differential scattering patterns and determining the bacterial sensitivity, or score S, to antibiotics.

There follows a list of components for the data processing circuit in FIG. 4 and selected components in FIG. 2. The memory functions as indicated in FIG. 4 are part of the memory 148 in FIG. 2. The other processing functions in FIG. 4 are part of the central processing unit 146 in FIG. 2.

ANALOG-TO-DIGITAL CONVERTER (119)

The analog-to-digital converter 119 is ZD 461 made by Zeltex, Inc.

DATA BUS 147

The data bus, as shown in FIG. 4, is constructed of "Tri-State ®" hex buffers, DM 8075, made by National Semiconductor Corporation, 2900 Semiconductor Drive, Santa Clara, California. A data bus is used to chain all signal sources (outputs) and signal sensor (inputs) together. The hex buffers isolate signal sources from the data bus in order that only one source be enabled to control the data bus at any given time. In FIG. 4, signal sources are analog-to-digital converter 119 and parallel adder 209. The inputs to $C_i$ memory 201 and $T_i$ memory 202 are signal sensors.

$C_i$ MEMORY 201 AND $T_i$ MEMORY 202

Both of the buffer memories 201 and 202 are comprised of six units of TMS 3101 LC each. The TMS 3003 is an M.O.S. dual 100 bit static shift Register made by Texas Instruments, Incorporated, Post Office Box 5012, Dallas, Texas 75222. Data inputs are directly connected to bipolar logic elements (TTL). The two phase clock inputs require discrete component level shifting to translate logical zero to minus twelve volts.

$C_i$ - $T_i$ AND ($C_i$ - $T_i'$) SUBTRACTOR 203

The subtractor 203 is essentially identical to adders 209, 211, 212, and 215 in that they incorporate parallel adders specifically SN 7483 N, a one-half byte parallel adder. The adder is made by Texas Instruments Incorporated, (T.I.), as well as many other integrated circuit manufacturers. Three such adders are required for each.

The carry-into-higher-order adder is determined by the carry out of the adjacent lower order adder. The carry-into-first adder is logical zero for addition and logical one for subtraction.

For subtraction, as in subtractor 203, the bits of the subtrahend are all complemented respectively by means of a hex inverter SN 7404 N made by T.I. Two units are required. The complemented data is coupled to the adder and the result is subtraction.

ABSOLUTE VALUE CONVERTER 204

This element consists of three half-byte parallel adders as described above and three quadruple exclusive-or gates, SN 7486 N by T.I. The purpose of converter 204 is to convert all negative numerical inputs to positive numbers and to leave all positive numerical inputs unaffected. Since binary two's complement numerical representation is used, any number is negated simply by complementing and then adding one. Only negative numbers are altered and therefore a conditional complementing element is required. The quadruple exclusive-or gate is used. On the exclusive-or gates, one input of each input pair is used for data input and the other input is used to control the conditional complementing. If the control is in the logical one state, the data is complemented. The data is unaltered if the control is in the logical zero state. One input of each input pair is connected in a chain so that all twelve bits of data are controlled by a common logical variable.

The control logical variable is applied to the carry input to the parallel adder circuit. Thus, if complementing occurs a carry is injected into the adder. All twelve bits of one of the two addition operpands are tied to logical zero. The twelve bites of the other operpand come from the conditional complementing circuit. Thus is provided the means to both conditionally complement the incoming data, and to conditionally add one to the complemented data. The control variable is determined by the sign bit of the incoming data. This is sufficient to convert signed two's complement data to strictly positive data.

SUMMER/TOTALIZER 205 AND $D_i$ SUMMER/TOTALIZER 207

Summer/Totalizers 205 and 207 are identical. They consist of the parallel adder circuit described in the paragraph regarding Subtractor 203 and twenty bits of semiconductor data storage. The summer/totalizers 205 and 207 require five parallel adders, SN 7483 N. The storage is implemented with two N 8202 N's made by Signetics Corporation in Sunnyvale, California. The 8202 is a ten-bit register consisting of ten bi-stable multivibrators with common clocks and common resets.

The sum outputs of the adder are the inputs to the register storage. The register outputs are used as augend inputs to the adder. The addend inputs to the adder convey the sequence of numbers to be totaled. Prior to totalizing, the zeroth partial sum is set to zero by the reset input to the 8202's. Each time the register clock is strobed a new partial sum is generated.

A MEMORY 206 AND B MEMORY 210

Both A memory 206 and B memory 210 are comprised of a pair of N 8202 N's each. The description of the N 8282 N is contained in the discussion regarding summer/totalizer 205.

$D_i$ DIVIDER 208

In the binary number system division by integer powers of 2 can be accomplished by shifting just as in the decimal number system; division by ten can be accomplished by shifting. There are no integrated circuits required to implement the function, indicated in the discussion of adder 209, if $N = 2^M$, M an integer.

ADDERS 209, 211, 212, AND 215

The adders 209, 211, 212, and 215 are specified in the discussion regarding subtractor 203.

BINARY CODED DECIMAL CONVERTER 213

The easiest way to convert a binary number to a binary coded decimal (BCD) number involves two types of counter. One counter starts with the binary number to be converted and counts down to zero. This counter operates in a pure binary mode. While this counter is decrementing, another counter is incrementing from zero upward. This second counter operates in the BCD mode. The first type of counter is implemented by cascading three SN 74191 N's (T.I.) together. The second type of counter is implemented by cascading three SN 7490 N's (T.I.). Three quadruple input nand gates SN 7420 N (T.I.) are used to sense the condition that the decrementing counter has reached zero. Prior to this conversion, the seven lower order bits are truncated to achieve convenient scaling of the sensitivity rating. This of course is an effective division by 128 as described in the discussion regarding divider 208.

S MEMORY 214

Memory 214 consists of shift register storage similar to that in the description regarding buffer memories 201 and 202. For this case, however, a hex 32 bit static shift register TMS 3112 (T.I.) is used.

DESCRIPTION AND EXPLANATION OF THE DATA PROCESSING WITH REFERENCE TO FIGS. 2 AND 4

In computing the algorithim for the preferred embodiment which, as noted above, is of the form $$S = A + 3B,$$

the first operation is concerned with computing the first term in accordance with the expression $$A = \sum_{i=1}^{m} |C_i - T_i|. \qquad \text{Eqn. (24)}$$

For this operation, referring now to FIG. 4, there is here illustrated a schematic block diagram of the data processing unit as it relates to the computation of the sensitivity score. Accordingly the analog-to-digital converter 119 is coupled to a buffer memory 201 where each $C_i$, i.e. each value log I of the intensity of the control scattered light at the $i^{th}$ angular location, is stored. The converter 119 is also coupled to a buffer memory 202 where each $T_i$, i.e. each value log I of the intensity of test scattered light at the $i^{th}$ angular location is stored. The output of the buffers 201 and 202 is coupled to a subtractor 203 where the computation ($C_i - T_i$) is achieved. The output of the subtractor 203 is coupled to an absolute value converter 204 which converts the $(C_i - T_i)$ into the absolute values $|C_i - T_i|$ so that each $$A_i = |C_i - T_i| \qquad \text{Eqn. (25)}$$

where $A_i$ = the contribution to the A term in Eqn (24) above at the $i^{th}$ angular location. The absolute values are coupled to a totalizer 205 which sums each $A_i$ to provide the total value for A as the output. The output A is then coupled to the A memory 206 where it is stored.

The next operation is concerned with the derivation of the B term from the expression $$B = \sum_{i=1}^{m} |C_i - T_i'| \qquad \text{Eqn. (26)}$$

where $$T_i' = T_i + D \qquad \text{Eqn. (27)}$$

and $$D = \frac{1}{n-q+1} \sum_{i=q}^{n} (C_i - T_i), \qquad \text{Eqn. (28)}$$

Where preferably $q = 19°$, $N = 82°$ and $N = n-q+1 = 64$. This number in binary notation represents division by a simple binary shift greatly simplifying the operation $$D = \frac{\sum_{i=19}^{82} D_i}{64} = \frac{\sum_{i=19}^{82} (C_i - T_i)}{64}. \qquad \text{Eqn. (29)}$$

The second calculation then is to determine D. Each increment $D_i$ is of the form $(C_i - T_i)$ as obtained from the subtractor 203. Each $D_i$ is coupled to a second totalizer 207 which sums the $D_i$ to produce in its output $\Sigma D_i$, which is then coupled to a divider 208 where $D_i$ is divided by N where $$N = (n-q+1). \qquad \text{Eqn (30)}$$

The output of the divider 208 then is D, which is coupled to an adder 209. Another input to the adder 209 is coupled from the test buffer memory 202 in the form of the $T_i$s. Each $T_i$ is added to D by the adder 209 to produce in its output $$T_i' = T_i + D. \qquad \text{Eqn (31)}$$

Each $T_i'$ is coupled back to the test buffer memory 202 and displaces the stored values of $T_i$ on a one-to-one basis until the buffer is filled. Each $T_i'$ is coupled from the memory 202 to the subtractor 203 where it is subtracted from its corresponding $C_i$ the difference is coupled to the absolute value converter 204. The output $B_i = |C_i - T_i'|$ of the converter 204 is coupled to the totalizer/summer 205. The summer 205 totalizes $\Sigma B_i =$ B which is then coupled from the summer 205 to the B memory 210. By introducing a binary shift at the input to the adder 211, the adder sees 2B at one input and B at another input to produce a sum of 3B. The output at adder 211 is coupled to a positive terminal of an adder 212 which derives another input from the A memory 206. The output of the adder 212 is $S = A + 3B$, which is coupled to a binary coded decimal converter 213. The output of the binary coded decimal converter 213 is coupled to the sensitivity score memory 214.

The quantity D is introduced at the input of an adder 215 which has an arbitrary positive value, L for example, representative of 500 mV applied to one terminal and D applied to the other. D is coupled directly also to the A memory 206. If D is less than zero, the A term is eliminated. If the output of the adder 215, D+L, is less than zero, it is coupled to the B memory 210 and the B term is eliminated. When that happens the resulting sensitivity score S is a special number like 00 which suggests, as noted above, that the bacteria are antibiotic dependent or the sample preparation faulty. The output score can be taken as 0–99 or 0–999 as a measure of the sensitivity of the bacteria to the antibiotic. In general a bacteria is sensitive to a given antibiotic if its score is greater than 40 and is insensitive or resistant if its score is less than 30. These scores are adjusted, however, for a specific antibiotic as necessary. It turns out to be necessary, however, in relatively few cases. For example, for penicillin > 40 is sensitive, < 40 is resistant while for ampicillin > 42 is sensitive, < 35 is resistant and $35 \leq S \leq 42$ is intermediate.

BACTERIAL SENSITIVITY TESTING PROTOCOL

In the co-pending Patent Application Ser. No. 139,366 a protocol was outlined involving the use of distilled water for both control bacteria and test bacteria. It has since been determined that the optimum preparation for the test involves the richest possible broth for the purpose of inducing a high metabolic rate for the bacteria. As the concentration of the broth constituents increases, however, the optical density of the medium increases. Such an increase is undesirable since it will mask out and so degrade the differential scattering patterns that their subsequent comparison becomes highly dependent on factors other than the bacteria themselves. Starting with standard infusion broth, it has been found that it is desirable to dilute it with two parts distilled water to each part infusion broth to yield a diluted broth having ⅓ the standard broth and ⅔ water.

The preferred protocol for practicing the invention involves the following steps:

(1) Prepare a prewarmed (38° C) four ml brain heart infusion broth culture by removing sufficient colonies from a young isolation culture to yield an optical density of about 0.1 to 0.15 at 640 nm (640 nm refers to the frequency of the light at which the optical density measurement is made in a standard spectrophotometer). NOTE: Isolation cultures may be used as soon as colonies are apparent, usually 8–18 hours for most typical clinical isolates.

Vortex mix the broth culture before making the optical density measurement.

(2) Incubate broth cultures 30–40 minutes.

(3) Prepare a cuvette tray and load it with 15 ml antibiotic/diluted broth solutions manually or using a dispenser. Incubate the tray with its antibiotic solutions at the same time as the broth is incubating (see Step 1) so that they are warmed to 38° prior to adding bacteria. One cuvette (as described and illustrated in the reference U.S. Pat. No. 3,701,620) should contain 15 ml diluted broth only — no antibiotic.

(4) After incubation of the broth culture and warming of the cuvette tray, remove both and add 0.3 ml of the bacterial broth (after vortex mixing) to each cuvette, including the control. Cap tightly.

(5) Incubate the inoculated tray for 90 ± 10 minutes at 38° C.

(6) Allow tray to sit about one minute and then place in the photometer of the invention.

The above protocol is applicable to both Gram-negative and Gram-positive bacteria. For the Gram-positive bacteria the correlation with conventional methods was found to exceed 98% for the representative antibiotics: ampicillin, choramphenicol, gentamicin, lincomycin, kanamycin, tetracycline, erythromycin, and penicillin. For the Gram-negative bacteria the following table illustrates typical results of their sensitivity to the antibiotics ampicillin, chloramphenicol, gentamycin, kanamycin, streptomycin and tetracycline carried out according to the procedure of the present invention. Parallel determinations using the disc diffusion (Kirby-Bauer) methods [Federal Register 36 (70), 6889 (1971) as amended in FR 37 (191), 20527 (1972)] were made in each case. A total of 100 strains of such Gram-negative pathogenic bacteria were tested. All pathogens tested were strains isolated from patients of the Royal Victoria Hospital in Montreal, or the Cottage Hospital in Santa Barbara.

| Pathogen | No. of strains tested | No. of tests carried out | No. of "Major Discrepancies" |
| --- | --- | --- | --- |
| Escherichia coli | 16 | 99 | 2 |
| Klebsiella sp. | 19 | 114 | 2 |
| Pseudomones aeruginosa | 11 | 69 | 1 |
| Proteus vulgaris | 10 | 66 | 2 |
| Enterobacter sp. | 14 | 90 | 5 |
| Proteus rettgeri | 1 | 6 | — |
| Proteus sp. | 1 | 9 | — |
| Proteus mirabillis | 14 | 90 | 5 |
| Citrobacter sp. | 2 | 12 | 1 |
| Serratia sp. | 12 | 72 | 2 |
| Totals | 100 (5) | 627 | 22 |

This set of trials indicates a Gram-negative correlation with the disc diffusion method of only 96.5%. A number of the discrepancies for both Gram-positive and Gram-negative strains, however, were resolved by tube dilutions in favor of the test of the present invention.

The test of the present invention is represented to be more accurate than the more time-consuming traditional disc diffusion procedure.

Using the protocol outlined above in the Gram-positive trails, (65) strains of *Staphylococcus aureus, Staphylococcus epidermidis* and *Streptococcus faecalis* were tested with the apparatus of the invention and found to be better than 98% correlated with the Kirby-Bauer results. Of the 65 strains 30 were taken from patients in The Royal Victoria Hospital in Montreal.

PROTOCOL — EVOLUTION

The development of the protocol outlined above is the result of extensive research carried on to optimize the process of the invention.

Initial experiments to determine antibiotic susceptibility of bacteria by differential light scattering were conducted by resuspending about $2 \times 10^8$ cells in broth to a concentration of about $4 \times 10^6$ cells per ml in water. The main purpose in using water was to stress the cells hoping that the antibiotics used to inhibit sensitive cells had weakened the cell wall and as a consequence cell disruption or some cell distortion (such as a change in cell size distribution) could be detected by changes in scattering patterns. The time periods chosen were 15 to 30 minutes, making it unlikely that growth would be a factor in determining an algorithm that would identify bacteria as resistant or sensitive to an antibiotic. By contrast, other workers have used complex broth media and turbidimetry for measuring sensitivity or resistance by lysis, growth or inhibition of bacterial populations treated with drugs. The time of incubation under these conditions is usually many hours and the method has inherent difficulties, principally that a single drug concentration is not effective against growth of all Gram-negative or Gram-positive organisms, even of the same species, isolated in the clinical laboratory.

The Kirby-Bauer method for determining the antibiotic susceptibility of bacteria in the presence of a continuous drug concentration gradient is done by placing a disc impregnated with a fixed concentration of drug on an agar plate (complex media) previously covered with a suspension of the organism to be tested. The size of the "inhibition zone" is a measure of the drug susceptibility of the organism. The two principal problems with this method are (1) determination of the zone size to be used in ascertaining drug susceptibility and its variation in repeat experiments with the same organism, and (2) the time required to complete the test usually from 6 to 20 hours.

The mode of action of cidal or static antibiotics generally requires the bacterial cell to be growing and complex media are most suitable for the growth of the bacteria most commonly isolated in the clinical laboratory. Most complex media, however, scatter considerable light. As a result, several complex media were tested and different concentrations of medium were used. The complex medium Brain Heart Infusion (BHI) was found to scatter considerably less light than several other media and 33% BHI was found not to interfere with the relative light intensity signal generated by exposing about $2 \times 10^6$ cells per ml to a red laser beam and observed by a detector rotated through the scattering angles from 30° to 130°. In addition, multiplication of bacteria in a medium at this dilution proceeds at a rate nearly identical to that of bacteria in a full strength broth, at least for the first few hours following innoculation.

The time of incubation of the cells with antibiotic is most suitable at 90 minutes in which period sufficient metabolism occurs in an untreated population. A comparison of the differential light scattering curves shows there is a change in the pattern for drug susceptible cell populations relative to the pattern of an untreated control. This growth in BHI medium with drug also exhibits a shift in maxima or in addition a washing out of the light scattering curve as a result of the alteration in the size distribution and/or structure of sensitive cells.

The added dimension of observing changes in the shape of light scattering curves with drug treatment has enabled Science Spectrum, Inc. to asertain whether an organism is sensitive or resistant to an antibiotic in 90 minutes, a considerable improvement with respect to the methodologies currently employed — the Kirby-Bauer test and tube dilution method.

MIC — MINIMUM INHIBITORY CONCENTRATION

Our experience indicates that the above-outlined protocol is useful for both Gram-negative and Gram-positive bacteria, varying only the drug concentrations.

In general, the score interpretations are the same for all drugs with a few very minor modifications for some species/drug combinations. This should be contrasted with the more conventional Kirby-Bauer disc diffusion test which requires a different interpretation for all drugs. A preferred embodiment of the present invention classifies all species sensitive if the term S exceeds 40, resistant if it is less than 30, and intermediate between these limits. These ranges could easily be modified by changing the logarithmic amplifier gain, changing the drug concentrations, or changing both.

It is often desirable for the treatment of bacterial infections with antibiotics for the attending physician to know not only what antibiotic will effectively inhibit the infecting bacteria, but, in addition, the minimum inhibitory concentration (MIC). Once the MIC level is known, the physcan can immediately determine an accurate therapeutic dose for treatment. This test is of particular importance for certain antibiotics that may produce toxic effects in the patient if the drug level is too high. Unfortunately conventional tube dilution techniques, by which means the MIC levels are usually determined requires another day to determine them. The preferred embodiment of the present invention may be used to determine these MIC values with considerable accuracy since our experience has shown that the number S produced by the instrument as a measure of antibiotic susceptibility bears a direct relationship to the antibiotic concentration used in the test specimen, as has already been mentioned. Accordingly if the number S and antibiotic concentration X be known, then the MIC value V may be derived therefrom by means of a relation of the form $$V(S,X) = \frac{hX}{f(S)},$$

where $h$ is a constant and $f$ is a function of S.

At present the preferred algorithm is based on the expression $$V(S,X) = \frac{hX}{S + \delta}, \text{ where}$$

S = antibiotic susceptibility for a given bacteria and antibiotic, and $\delta$ = constant that varies with the antibiotic.

BIOASSAY

Many clinical and laboratory analyses are concerned with the quantative determination of the chemotherapeutic drug levels in serum and tissue. On the one hand, for certain types of antibiotics, it becomes extremely important for the attending physician to be able to monitor the drug level in the patient serum, especially if he has already determined the MIC level needed to combat a particular infection. Since some antibiotics have toxic side effects, it becomes extremely important to maintain drug levels below levels toxic to the patient but above levels inhibitory or lethal to the infection-causing bacteria. Serum and urine level assays are also important for monitoring a large class of anti-cancer drugs used to arrest malignant cells for a variety of cancers. Most anti-tumor drugs are also highly toxic to the patient's normal cells, requiring close attention to the serum levels attained in the patient during treatment. The development of chemotherapeutic drugs in the laboratory usually requires animal experimentation and its associated determination of serum drug levels. Another area of particular importance relates to the need to determine the presence and quantity of various bio- chemicals such as antibiotics in meats, poultry, and other food products because of the health hazard these chemicals could present to the consumer.

One of the most widely used techniques for the assay of biochemicals in serum, urine and food products is the bioassay technique which is very similar to the disc diffusion antibiotic susceptibility test. A calibrated known bacterial strain is spread over the surface of an agar plate. A small sample of serum, urine, or food extract is placed in a well cut into the plate, or on a small cardboard disc placed on the plate. The bacterial strain is chosen such that it is sensitive to the particular agent or chemical whose assay is sought. After about 20 hours of incubation, the zone diameter surrounding the well or disc is measured and, on the basis of previous calibrations, is used quantatively to determine the amount of the agent present in the well or on the disc. From knowledge of the volume of fluid used in the assay, the drug concentration in the sample source may be determined.

By the same means, unknown drugs are often presumtively identified. However, for this situation, several replicate plates must be prepared each of which involves the use of a different bacterial strain sensitive to different drugs.

The major problems with the conventional clinical bioassay techniques described above are that they are slow (6–24 hours), not particularly accurate, require considerable labor and space, and often require exceptional skills for their performance. For critically-ill patients, the time factor often precludes using any such bioassay for serum level determination. The labor intensive aspects make food bioassays prohibitive thereby requiring that the monitoring agencies sample only an extremely small fraction of the food products that reach the consumer.

It will be appeciated that the photometer of the present invention is capable of performing various bioassay tests rapidly and economically using calibrated bacterial strains whose response to various chemical agents may be represented in terms of the scores produced by the photometer. As an example, consider the assay of meat and poultry products for the presence of antibiotics, sulphonomides, and nitrofurans.

A screening methodology would be a version of the standard procedure developed by the FDA, i.e. specimens would be tested against a set of organisms which delineate the assigned drugs on the basis of their drug susceptibilities. This procedure is illustrated in the matrix of Table I which follows the practice used by the USDA [USDA Microbiology Laboratory Guidebook, Washington 1974] in determining the antibiotic residues in animal tissues. This table contains the four antibiotics, a sulphonamide and a nitrofuran.

TABLE I

| DRUG SCREENING MATRIX | | | | | | |
|---|---|---|---|---|---|---|
| Science Spectrum Species | Tetra-cycline | Nec-mycin | Strep-to-mycin | *Peni-cillin | **Sul-phonamide | Nitro-furan |
| A | R | R | R | S | R | R |
| B | S | R | R | R | R | R |
| C | R | R | S | R | R | R |
| D | R | S | R | R | R | R |
| E | R | R | R | R | R | S |
| F | R | R | R | R | S | R |

R = resistant, S = susceptible
*Penicillinase-treated specimen may be used also.
**PABA-treated specimen may be used also.

For the case of penicillin, it is often useful to use duplicate extracts, to one of which penicillinase is added. Similarly, a duplicate PABA-tested extract of a suspected sulphonamide-bearing tissue extract can simplify the screening process.

Note that species A, B, C and D have identical antibiograms to the USDA recommended strains (for cit.) *Sarcina lutea* (ATCC 9341A), *Bacillus cereus* (ATCC 11778), B *subtiles* (ATCC 6633), and *Staphylococcus epidermidis* (ATCC 12228), respectively. Many other strains may be used for this bioassay test of the present invention including many which are more susceptible to the listed drugs than the USDA set, are more easily cultured, and less subject to spontaneous mutations. In addition to the six reference strains, it is useful to use a single strain, highly susceptible to all of the referenced drugs, thereby permitting the rapid screening of negative samples and several strains are already in use.

The technique for screening and assaying with the photometer of the present invention would consist, in broad outline (based upon experience with other phases of antimicrobial testing), of setting up a set of six cuvettes and a similar number of controls, each containing equal aliquots of broth from the six organisms (of Table I) in their exponential phase. The screening of negative specimens would, of course, precede this specification assay. The sample specimens would, in a preferred embodiment, be prepared by using a small press to squeeze a sufficient extract (of the order of 0.1 mm) fron a few grams of tissue. Particulate matter within the sample would then be removed by filtration or centrifugation. Serum or urine specimens could be used directly after particulate filtration. To each of the six test cuvettes would be simultaneously added six equal aliquote of the specimen under investigation, and the entire set would then be incubated for 90 minutes. After removal of the set from the incubator and dilution of the contents in each cuvette by 15 ml of distilled water, a simultaneous DLS test of each cuvette would be taken. The resultant 'scores' relative to the controls will indicate the presence or absence of the drugs in the specimens, and, if the concentrations of drugs and bacteria are within a specified range, these scores would then be used to derive quantitative measures of the drug concentrations as described in the disclosure on MIC determinations. Explicit scores for each drug might be generated over certain critical ranges and such quantitative results might be supplemented by qualitative classifications at the endpoints. For example, for tetracycline explicit numerical results might only be required for concentrations between 0.01 ug/ml and 50 ug/ml. Any detectable concentrations lying outside this range might be indicated simply as greater than 50 ug/ml or less than 0.01 ug/ml.

Tests already conducted in the laboratories of the inventor using the methods employed in the photometer of the invention have already yielded detection of the following levels of drugs: tetracycline, 0.02 ug/ml; neomycin, 0.05 ug/ml; streptomycin, 0.05 ug/ml; penicillin, 0.002 ug/ml. These minimum detectable levels can certainly be reduced by a factor of ten and these assay levels achieved should be contrasted with those presented (for tissue assay) in the USDA Microbiology Laboratory Guide (loc. cit.), viz. tetracycline, 0.025 ug/ml; neomycin, 0.124 ug/ml; streptomycin, 0.05 ug/ml; penicillin, 0.0063 ug/ml.

While there has hereinbefore been presented what are at present considered to be the preferred embodiment or processes, it will be apparent to those of ordinary skill in the art that many modifications and variations may be made therefrom without departing from the true spirit and scope of the invention.

All such variations and modifications, therefore, are considered to be a part of the invention.

What is claimed is:

1. A process for determining the minimal inhibitory concentration (MIC) of a given bacterial sample to a selected chemical agent comprising the steps of:
   A. preparing from said given bacterial sample a bacterial control sample in a medium promoting growth of bacteria;
   B. incubating said bacterial control sample for a period of time sufficient for metabolism to occur;
   C. inserting said sample into the path of an incident narrow, substantially monochromatic beam of radiant energy;
   D. measuring the intensity of radiant energy scattered by said sample at plurality of angular locations about said sample relative to the direction of said incident beam sufficient to derive a control differential scattering pattern produced by said sample;
   E. preparing from said given bacterial sample a bacterial test sample including a predetermined concentration, X, of a selected chemical agent in a medium promoting growth of bacteria;
   F. incubating said bacterial test sample for substantially the same period of time and under substantially the same conditions as the bacterial control sample;
   G. inserting said test sample into said beam path;
   H. measuring the intensity of radiant energy scattered by said test sample at substantially the same angular locations about said test sample to derive a test differential scattering pattern produced by said test sample;
   I. comparing said test and control patterns to yield a score, S, indicative of the effects of the chemical agent upon bacterial growth and upon bacterial morphology; and,
   J. determining the MIC value, V (S, X), from the score, S, and the predetermined concentration, X, of the selected chemical agent.

2. The process of claim 1 where the chemical agent is an antibiotic.

3. The process of claim 1 where the MIC value, V, is derived from the score S and the concentration X substantially in accordance with the expression $$V = \frac{hX}{f(S)}$$

or any of its algebraic equivalents where h is a constant characteristic of the chemical agent and $f(S)$ is a function of the score S that is an increasing function with increasing susceptibility of the bacterial sample to lower concentrations of the chemical agent.

4. The process of claim 3 where:

$$f(S) = S + \delta$$

or any of its algebraic equivalents where $\delta$ is a constant characteristic of the chemical agent.

5. The process of claim 1 where the concentration of bacteria in the bacterial test sample is known relative to the concentration of bacteria in the control samples and adjusting the determination to compensate for any substantial difference between these concentrations.

6. The process of claim 1 where the bacterial test and control samples are prepared in a growth medium made by diluting a standard liquid bacterial growth medium.

7. A process for screening a test specimen for the presence of a particular chemical agent comprising the steps of:
   A. preparing a chemical suspension from a sample known to be free of said particular chemical agent by combining in a bacterial growth medium said sample with exponential growth phase bacteria whose sensitivity response to said chemical agent is known;
   B. incubating said control suspension for a predetermined period of time sufficient for metabolism to occur;
   C. inserting said control suspension into the path of an incident narrow, substantially monochromatic beam of light;
   D. measuring the intensity of light scattered by said control suspension at a plurality of angular locations about said control suspension to derive a control differential scattering pattern produced by said control suspension;
   E. preparing a test suspension from a test sample to be screened for said particular chemical agent by combining in a bacterial growth medium said test sample with substantially the same type of bacteria in exponential growth phase as used to prepare the control suspension;
   F. incubating said test suspension for substantially the same period of time and under substantially the same conditions as the control suspension;
   G. inserting said test suspension into said beam path;
   H. measuring the intensity of light scattered by said test suspension at substantially the same angular locations about said test suspension to derive a test differential scattering pattern produced by said test suspension;
   I. comparing said test and control patterns to yield a score, S, indicative of the effects of the test sample on the growth and morphology of the test bacterial suspension relative to the control bacterial suspension; and,
   J. determining from the magnitude of said score the presence of said particular chemical agent in the test sample.

8. A process for quantifying the amount of a chemical agent in a test specimen comprising the steps set forth in the process of claim 7 including:
   A. comparing said test and control patterns to yield a score, S, indicative of the changes of the test pattern relative to the control pattern;
   B. determining the functional response, $f(S)$, of the bacterial specimen to said chemical agent; and
   C. determining from the score, S, and the functional response of the bacterial specimen to the chemical agent the concentration, X, of the chemical agent in the test specimen.

9. The process of claim 8 where the amount of the chemical agent, X, is derived from the score, S, and the functional response, $f(S)$, substantially in accordance with the expression $X = cf(S)$ or any of its algebraic equivalents where $c$ is a constant characteristic of the chemical agent.

10. The process of claim 9 where:

$$f(S) = S + \delta$$

or any of its algebraic equivalents where $\delta$ is a constant characteristic of the chemical agent.

11. The process of claim 7 in which the test specimen is obtained by extracting liquid from a tissue sample.

12. The process of claim 7 including the steps of diluting the incubated control suspension and the incubated test suspension with the same diluent and by substantially the same amounts before inserting them into said light beam path.

13. A process for measuring the response of antibodies to their environment, comprising the steps of:
   A. preparing an antibody control sample;
   B. inserting said control sample into the path of an incident narrow, substantially monochromatic beam of light;
   C. measuring the intensity of light scattered by said sample at a plurality of angular locations about said sample relative to the direction of said incident beam sufficient to derive a control differential scattering pattern produced by said sample;
   D. preparing an molecular test sample including a selected environmental change relative to said control sample;
   E. inserting said test sample into said beam path;
   F. measuring the intensity of light scattered by said test sample at substantially the same said angular locations about said test sample to derive a test differential scattering pattern produced by said test sample; and
   G. comparing said control and test patterns to determine a selected relative difference therebetween, said difference providing an indication of the response of said antibodies to said selected environmental change.

14. The process of claim 13 wherein said molecules are antibodies and said environment may include antigens, the determination detecting the presence of antigens in the selected environment.

15. The process of claim 14 wherein the antibodies are contained in an aliquot of human serum and the antigen is a commercially produced reagent.

16. The process of claim 13 wherein the measurements of the differential scattering patterns are performed at a plurality of different times on at least the test sample.

17. The process of claim 13 wherein said environment may include viruses, the determination detecting their presence in the selected environment.

18. The process of claim 13 wherein said environment may include particles having a natural affinity to the molecules, the determination detecting their presence in the selected environment.

19. The process of claim 18 wherein said particles are molecules.

20. A process for quantitating the response of biologically derived molecules to their environment, comprising the steps of:
   A. preparing a set of molecular control samples including a reference sample, each in a different environment,
   B. inserting said control samples sequentially into the path of an incident, narrow, substantially monochromatic beam of light;
   C. measuring the intensity of light scattered by each control sample at a plurality of angular locations about said control sample relative to the direction of said incident beam sufficient to derive a set of control differential scattering patterns produced by said control samples;

D. comparing said patterns relative to the reference control sample so as to derive a score, S, for each control environment condition and therefrom a set of scores deriving a response function $f(S)$;

E. preparing a molecular test sample in a test environment;

F. inserting said test sample into the path of incident, narrow, substantially monochromatic beam of light;

G. measuring the intensity of light scattered by said test sample at substantially the same said angular locations about said test sample to derive a test differential scattering pattern produced by said test sample;

H. comparing said test pattern with the previously measured reference control patterns to derive a score, S, indicative of the test environment; and, I. comparing said score, S, with said control response function, $f(S)$, to derive and quantitate molecular response to the test environment.

21. The process of claim 20 where the molecules are antigens the control environments contain antibodies at known concentrations, and where the test environment may contain antigens at an unknown concentration.

22. The process of claim 21 wherein the test environment includes serum, the antigens being contained in an aliquot of said serum.

23. The process of claim 20 wherein the measurements of the differential scattering patterns are performed at a plurality of different times on at least the test sample.

24. The process of claim 20 wherein said environment may include viruses, the determination detecting their presence in the selected environment.

25. The process of claim 20 wherein said environment may include particles having a natural affinity to the antigens, the determination detecting their presence in the selected environment.

26. The process of claim 20 wherein each of the control and test samples are allowed to interact with their environment for substantially the same time and under substantially the same conditions prior to their insertion in said light beam.

* * * * *